US010206753B2

(12) United States Patent
Tarlian, Jr.

(10) Patent No.: US 10,206,753 B2
(45) Date of Patent: Feb. 19, 2019

(54) SELF-WETTING SURGICAL GLOVE

(71) Applicant: Henry S. Tarlian, Jr., Scottsdale, AZ (US)

(72) Inventor: Henry S. Tarlian, Jr., Scottsdale, AZ (US)

(*) Notice: Subject to any disclaimer, the term of this patent is extended or adjusted under 35 U.S.C. 154(b) by 1117 days.

(21) Appl. No.: 13/712,768

(22) Filed: Dec. 12, 2012

(65) Prior Publication Data
US 2014/0157485 A1 Jun. 12, 2014

(51) Int. Cl.
*A61B 42/10* (2016.01)
*A61B 42/00* (2016.01)
*A61B 17/00* (2006.01)

(52) U.S. Cl.
CPC .............. *A61B 42/10* (2016.02); *A61B 42/00* (2016.02); *A61B 2017/00942* (2013.01)

(58) Field of Classification Search
CPC .......... A41D 19/0079; A41D 19/01594; A61B 19/045; A61B 2019/103; A61B 19/34; A61B 42/10; A61B 42/00; A61B 2017/00942
See application file for complete search history.

(56) References Cited

U.S. PATENT DOCUMENTS

| 1,558,930 | A | * | 10/1925 | Schuck | 239/529 |
| 2,405,154 | A | * | 8/1946 | Logan | 401/7 |
| 3,121,877 | A | * | 2/1964 | Gintner | 2/159 |
| 3,883,897 | A | * | 5/1975 | Lefkowitz et al. | 2/161.6 |
| 4,003,865 | A | * | 1/1977 | Nowak et al. | 524/44 |
| 4,087,675 | A | * | 5/1978 | Sansonetti | 604/292 |
| 4,848,246 | A | * | 7/1989 | Rosen | 109/25 |
| 5,169,251 | A | * | 12/1992 | Davis | 401/7 |
| 5,378,529 | A | * | 1/1995 | Bourdeau | 428/36.1 |
| 5,681,574 | A | * | 10/1997 | Haber et al. | 424/402 |
| 6,170,532 | B1 | * | 1/2001 | Campbell | 138/126 |
| 6,513,998 | B1 | * | 2/2003 | Barry | 401/7 |
| 2002/0017310 | A1 | * | 2/2002 | Gruenbacher et al. | 132/320 |
| 2004/0060095 | A1 | * | 4/2004 | Bradbury | 2/159 |
| 2011/0046544 | A1 | * | 2/2011 | Beeley | 604/23 |

* cited by examiner

*Primary Examiner* — Khaled Annis
(74) *Attorney, Agent, or Firm* — Sheppard Mullin Richter & Hampton LLP

(57) ABSTRACT

A moisture dispensing system, and its method of use, are presented for wetting a medical device prior to insertion into a patient. The moisture dispensing system comprises: a fluid reservoir configured for attachment to the dorsal aspect of a surgical glove when worn by a wearer; and an absorbent pad configured for attachment to the palmar aspect of a digit of said surgical glove when worn by a wearer, wherein said absorbent pad is in fluid communication with said fluid reservoir.

23 Claims, 2 Drawing Sheets

SELF-WETTING SURGICAL GLOVE

FIELD OF THE INVENTION

The invention broadly relates to a glove for use during surgery, and more particularly to surgeries involving medical devices coated with a moisture activated hydrophilic coating.

BACKGROUND OF THE INVENTION

It is well known in the practice of medicine and veterinary science that instruments inserted into the body should have a low coefficient of friction between the instrument and surrounding tissues to facilitate ease of insertion and also to minimize trauma to the tissues surrounding the insertion tract. In addition, guidewires are often used to facilitate insertion of several interventional medical instruments, such as catheters, stents, etc. Guidewires and interventional medical instruments are often coated with hydrophilic coatings that include a water soluble polymer. These hydrophilic polymers are lubricious coatings that are activated by contact with a wetting fluid, such as sterile water or saline, to provide a slippery surface when activated. Thus, hydrophilic coated guidewires and interventional medical instruments have a low coefficient of friction, provided that they are sufficiently wet.

A disadvantage of such hydrophilic coatings is the requirement that they be continuously wet to maintain their lubricity during use. Furthermore, if such a coated instrument is first wetted and then allowed to dry, the coated surface passes through a phase where the surface becomes somewhat tacky and has a much higher coefficient of friction as compared to the end phase when the coating has completely dried. It is therefore essential to ensure that those parts of the instrument which lie outside the body are wet immediately before insertion.

To maintaining sufficient wetness of a hydrophilic coated surface, it is currently necessary for a surgical assistant to keep the coated medical device (guidewire, catheter, etc.) wet while the physician manipulates the device. However, it is often difficult for a physician and an assistant to coordinate wetting and manipulation of the device during the procedure. Moreover, wiping such coated devices with wet gauze pads (as is often the case) can leave a residue which adheres to the surface of such devices.

SUMMARY OF THE INVENTION

In one aspect, a moisture dispensing system for wetting a medical device to be inserted into a subject during surgery is presented. The moisture dispensing system comprises: a fluid reservoir configured for attachment to the dorsal aspect of a surgical glove when worn by a wearer; and an absorbent pad configured for attachment to the palmar aspect of a digit of said surgical glove when worn by a wearer, wherein the absorbent pad is in fluid communication with the fluid reservoir.

In some embodiments, the moisture dispensing system comprises distinct absorbent pads configured for attachment to the palmer aspect of each of a plurality of digits, such as two, three, four, or five digits of said surgical glove. In some embodiments, the moisture dispensing system comprises distinct absorbent pads configured for attachment to the palmer aspect of each of the second, third, and fourth digits of said surgical glove.

In some embodiments, an absorbent pad is configured for attachment to the palmer aspect of a digit of said surgical glove such that the absorbent pad is found in the region of the second and third metacarpophalangeal (MP) joints of a wearer.

In some embodiments, the moisture dispensing system further comprises fluid conduit extending from the fluid reservoir to an absorbent pad. In some related embodiments, the fluid conduit comprises polyvinyl chloride tubing, polyisoprene rubber tubing, or nitrile rubber tubing. In some related embodiments, fluid conduit comprises a flexible solid material through which fluids are capable of passing by wicking action.

In some embodiments, the fluid reservoir comprises an injection port for introduction of a fluid into the fluid reservoir. In some embodiments, the fluid reservoir is capable of containing between about 5 ml to 50 ml of fluid, such as between about 5 ml to 25 ml, such as between about 10 ml to 20 ml. In some embodiments, fluid contained in the fluid reservoir flows to an absorbent pad without the aid of a pump.

In some embodiments, the moisture dispensing system is sterile.

In another aspect, a moisture dispensing glove is presented, the moisture dispensing glove comprising: a glove having five digits; a fluid reservoir located on the dorsal aspect of the glove; and an absorbent pad attached to the palmar aspect of a digit, wherein the absorbent pad is in fluid communication with the fluid reservoir.

In some embodiments, the moisture dispensing glove comprises distinct absorbent pads attached to the palmer aspect of each of a plurality of digits, such as two, three, four, or five digits. In some embodiments, the moisture dispensing glove comprises distinct absorbent pads are attached to the palmer aspect of each of the second, third, and fourth digits.

In some embodiments, an absorbent pad is attached to the palmer aspect of a digit such that the absorbent pad is found in the region of the second and third metacarpophalangeal (MP) joints of a wearer.

In some embodiments, the moisture dispensing glove further comprises fluid conduit extending from the fluid reservoir to an absorbent pad. In some related embodiments, the fluid conduit comprises polyvinyl chloride tubing, polyisoprene rubber tubing, or nitrile rubber tubing. In some related embodiments, fluid conduit comprises a flexible solid material through which fluids are capable of passing by wicking action.

In some embodiments, the fluid reservoir comprises an injection port. In some embodiments, the fluid reservoir is capable of containing between about 5 ml to 50 ml of fluid, such as between about 5 ml to 25 ml, such as between about 10 ml to 20 ml. In some embodiments, fluid contained in the fluid reservoir flows to an absorbent pad without the aid of a pump.

In some embodiments, the moisture dispensing glove is sterile.

In another aspect, methods of inserting a medical device into a patient are presented. These methods comprise: wetting a medical device with a moisture dispensing glove immediately prior to inserting the medical device into a patient; wherein the moisture dispensing glove comprises a glove having five digits, a fluid reservoir located on the dorsal aspect of the glove, and an absorbent pad attached to the palmar aspect of a digit; wherein the fluid reservoir contains a sterile fluid, and the absorbent pad is in fluid communication with the fluid reservoir.

In some embodiments, the medical device being inserted into a patient comprises a hydrophilic coating. In some embodiments, the medical device being inserted into a patient is a guidewire or interventional medical device. In some embodiments, the medical device being inserted into a patient is a guidewire, catheter, balloon, or stent.

In some embodiments, the moisture dispensing glove comprises distinct absorbent pads attached to the palmer aspect of each of a plurality of digits, such as two, three, four, or five digits. In some embodiments, the moisture dispensing glove comprises distinct absorbent pads attached to the palmer aspect of each of the second, third, and fourth digits.

In some embodiments, an absorbent pad is attached to the palmer aspect of a digit such that the absorbent pad is found in the region of the second and third metacarpophalangeal (MP) joints of a wearer.

In some embodiments, the moisture dispensing glove further comprises fluid conduit extending from the fluid reservoir to an absorbent pad.

In some embodiments, the fluid reservoir comprises an injection port. In some embodiments, the fluid reservoir is capable of containing between about 5 ml to 50 ml of fluid, such as between about 5 ml to 25 ml, such as between about 10 ml to 20 ml. In some embodiments, fluid contained in the fluid reservoir flows to an absorbent pad without the aid of a pump.

In some embodiments, the moisture dispensing glove is sterile.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

DETAILED DESCRIPTION

Figure 1:
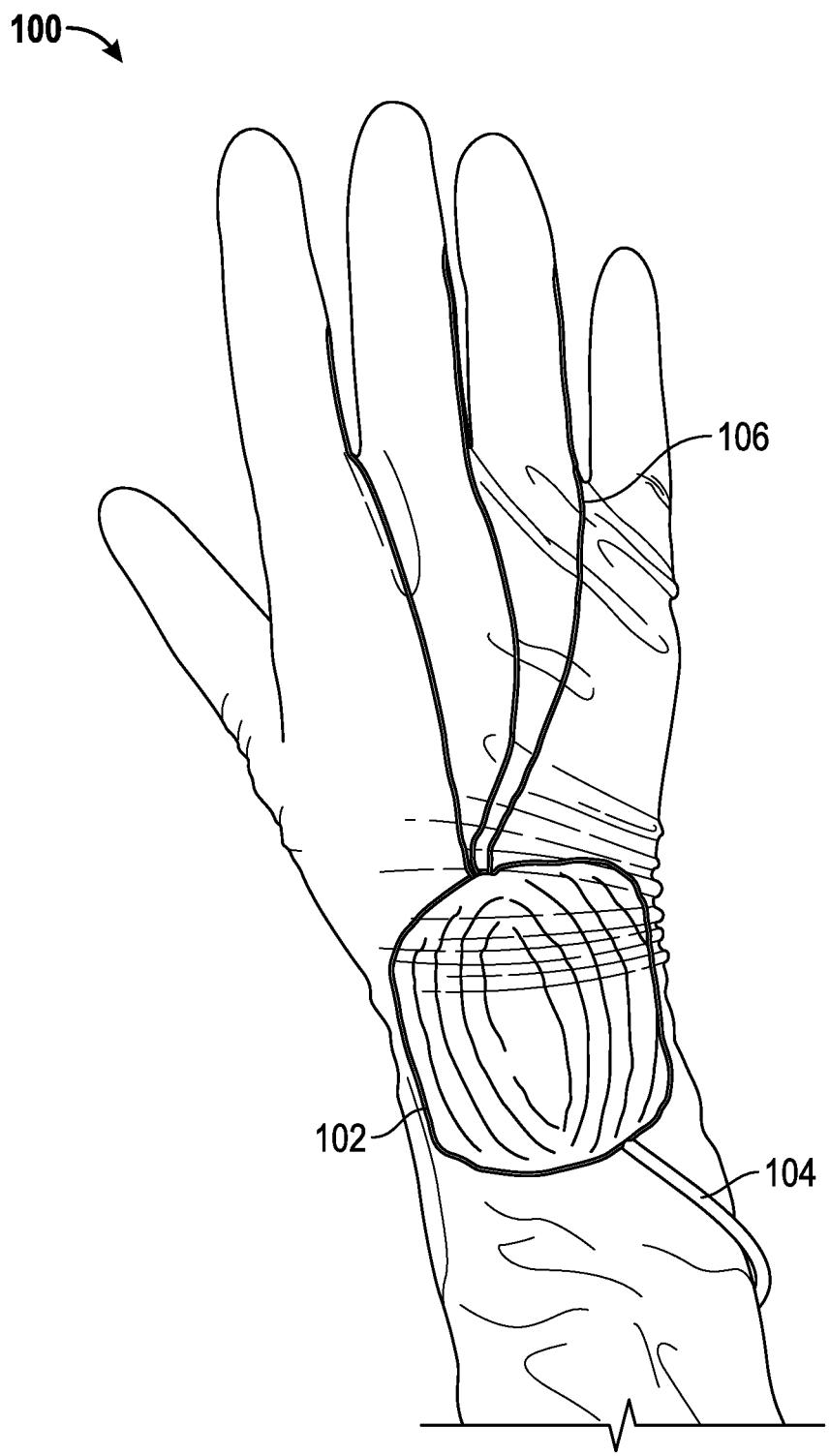
FIG. 1 is distal view of an exemplary embodiment of a self-wetting sterile glove.

In the following paragraphs, the present invention will be described in detail by way of example with reference to the attached drawings. Throughout this description, the preferred embodiment and examples shown should be considered as exemplars, rather than as limitations on the present invention. As used herein, the "present invention" refers to any one of the embodiments of the invention described herein, and any equivalents. Furthermore, reference to various feature(s) of the "present invention" throughout this document does not mean that all claimed embodiments or methods must include the referenced feature(s).

As described above, guidewires and interventional medical devices are often coated with hydrophilic coatings that include a water soluble polymer. These hydrophilic polymers are lubricious coatings that are activated by contact with a wetting fluid, such as sterile water or saline, to provide a slippery surface when activated. Thus, hydrophilic coated guidewires and interventional medical instruments have a low coefficient of friction, provided that they are sufficiently wet.

A disadvantage of such hydrophilic coatings is the requirement that they be continuously wet to maintain their lubricity during use. Furthermore, if such a coated instrument is first wetted and then allowed to dry, the coated surface passes through a phase where the surface becomes somewhat tacky and has a much higher coefficient of friction as compared to the end phase when the coating has completely dried. It is therefore essential to ensure that those parts of the instrument which lie outside the body are wetted immediately before insertion.

By way of example, a guidewire is commonly used for inserting and exchanging catheters within the vascular system. The technique for inserting a catheter within the vascular system consists of first establishing a path through the patient's skin into a blood vessel, as by the use of an introducer needle. A guidewire is then inserted through the introducer needle and guided into the blood vessel until the distal tip of the guidewire has advanced to the point of interest. The introducer needle may then be removed, and a catheter is then advanced over the proximal end of the guide wire, through the skin entry point, and along the blood vessel until the distal tip of the catheter reaches the end of the guidewire. The guidewire may then be withdrawn, leaving the catheter in place. If such a guidewire has a hydrophilic coating, it is necessary to wet the guidewire before inserting the proximal end of the guide wire into the distal end of the catheter. However, if the guidewire begins to dry before the catheter has been fully advanced thereover, the hydrophilic coating can become tacky and resist further advancement of the catheter.

Guidewires are also commonly used for exchanging catheters in the vascular system. The technique for exchange consists of placing the guidewire through a catheter already in the vascular system and removing the catheter from the blood vessel by sliding it over the guide wire and removing the catheter therefrom. The portion of the guidewire that lies outside the patient may be wiped with a wet sterile gauze pad to remove residual blood after a catheter is withdrawn thereover. A new catheter is threaded over the guidewire into the vascular system until the distal end of the guidewire is reached and the guidewire is then removed.

If a hydrophilic guidewire is used to perform this procedure, then certain precautions are necessary. When the first catheter is withdrawn during such a catheter exchange operation, the portion of the guidewire that is visible outside the catheter must be wetted to maintain lubricity; otherwise, as the catheter is withdrawn, the frictional force developed between the catheter and guidewire will cause both the catheter and the guide wire to be removed from the blood vessel, resulting in a loss of access to the vascular system.

Once the first catheter has been successfully removed from the guidewire, and the second catheter is to be threaded over the guidewire, the portion of the guidewire lying outside the body must be wetted once again; otherwise, it may be very difficult to thread the second catheter over the guidewire.

By way of a further example, catheters are often introduced into a blood vessel through a sheath previously placed in a blood vessel or organ. In other cases, catheters are directly introduced through the patient's skin without the use of a sheath. If the catheter includes a hydrophilic coating over its outer surface, the catheter must be wetted prior to insertion through such a sheath or through the patient's skin. Even if the catheter is initially wetted, a delay of only one or two minutes during the insertion procedure can be enough to result in increased friction when the catheter is advanced through the sheath or through the patient's skin, making it much more difficult to pass the catheter into the patient's body.

In view of the requirement of maintaining sufficient wetness of a hydrophilic coated surface, it is currently necessary for a physician to require an assistant to keep the coated medical device (guidewire, catheter, etc.) wet while the physician manipulates the device. However, it is often difficult for a physician and an assistant to coordinate wetting and manipulation of the device. Moreover, wiping such coated devices with wet gauze pads (as is typical) can leave a residue which adheres to the surface of such devices.

Described herein are devices and methods that facilitate wetting of medical devices during surgery. In particular, a moisture dispensing sterile hand-covering device (i.e., a moisture dispensing glove) comprising a fluid reservoir in fluid communication with a sponge-like substance located on one or more fingers of the device, and methods of using the same, are described. It is intended that the devices described herein are worn by a physician during surgery, thus allowing the physician to wet and manipulate a medical device simultaneously.

The moisture dispensing glove of the instant invention comprises a fluid reservoir on the dorsal aspect of the device. In some embodiments, the fluid reservoir is located such that when the moisture dispensing glove is worn, the reservoir sits over the wrist of the wearer. The fluid reservoir comprises an injection port to allow infusion of water, saline and/or other sterile liquid. In some embodiments, the reservoir has a capacity of up to about 5 ml, 10 ml, 25 ml, 50 ml, or more of liquid. In some embodiments, the reservoir can contain between about 5 ml to 50 ml of fluid, such as between about 5 ml to 25 ml, such as between about 10 ml to 20 ml The moisture dispensing glove of the instant invention further comprises one or more absorbent pads in fluid communication with the fluid reservoir. The one or more absorbent pads are located on the palmar aspect of the digits of the moisture dispensing glove. In some embodiments, the moisture dispensing glove comprises sponge-like pads located on one, two, or three fingers. In some embodiments, the absorbent pads are located on one or more of the second, third, and fourth digits. In some embodiments, the absorbent pads are located on all three of the second, third, and fourth digits.

The absorbent pads may be located at any position on the palmar aspect of the digits, so long as the they are accessible while the wearer is handling a medical device to be inserted into a patient (guidewire, catheter, etc.). However, it may be desirable that the absorbent pads not cover the fingertips, so as to not interfere with the wearers tactile acuity or otherwise impede performance of fine manipulations during insertion of the medical device. For instance, in some embodiments the absorbent pads are located in the region of the second and third metacarpophalangeal (MP) joints. This location is near enough to the fingertips to allow for easy access while manipulating a coated medical device, yet does not cover the fingertips.

The absorbent pads may be made of any suitable sterilizable sponge-like material. For instance, the absorbent pads may comprise a polyurethane or polyether foam, or any other foam suitable for medical device use.

The absorbent pads and fluid reservoir may be connected by any number of means so long as the fluid in the fluid reservoir is continuously accessible to the absorbent pads. For instance, flexible fluid conduit may connect the fluid reservoir to each absorbent pad. In such embodiments, a flexible fluid conduit may extend along the dorsal aspect of the glove to the base of the fingers, where a conduit may then be arranged to extend along the side of a digit, and eventually be directed to the palmar aspect of the digit to contact an absorbent pad.

In some embodiments, the flexible fluid conduit may be made of any suitable flexible, sterilizable material. For instance, the flexible fluid conduit may be polyvinyl chloride tubing, polyisoprene rubber tubing, nitrile rubber tubing, or tubing made of similar materials suitable for use in a medical device.

In other embodiments, the absorbent pads and fluid reservoir may be connected by a flexible solid material through which fluids are capable of passing, e.g. via wicking action. For instance, such a flexible solid material may comprise a fibrous cellulosic material similar to that found in laminar flow test strips. In some of these embodiments, one or more surfaces of the flexible solid material may be coated such that the coated surfaces are water and/or microbe impermeable. In other of these embodiments, the flexible solid material may be disposed within a water and/or microbe impermeable sheath, such as polyvinyl chloride tubing, polyisoprene rubber tubing, nitrile rubber tubing, or tubing made of similar materials suitable for use in a medical device.

In some embodiments, each absorbent pad draws fluid from the fluid reservoir without the aid of a pump or other external device. In some embodiments, this happens via wicking action through a fluid conduit. In these embodiments, each absorbent pad continuously draws fluid and remains wet so long as fluid remains in the reservoir. This allows the operator to continuously wet a coated medical device as they work, ensuring reduced friction and preventing binding of the coated medical device.

Figure 2:
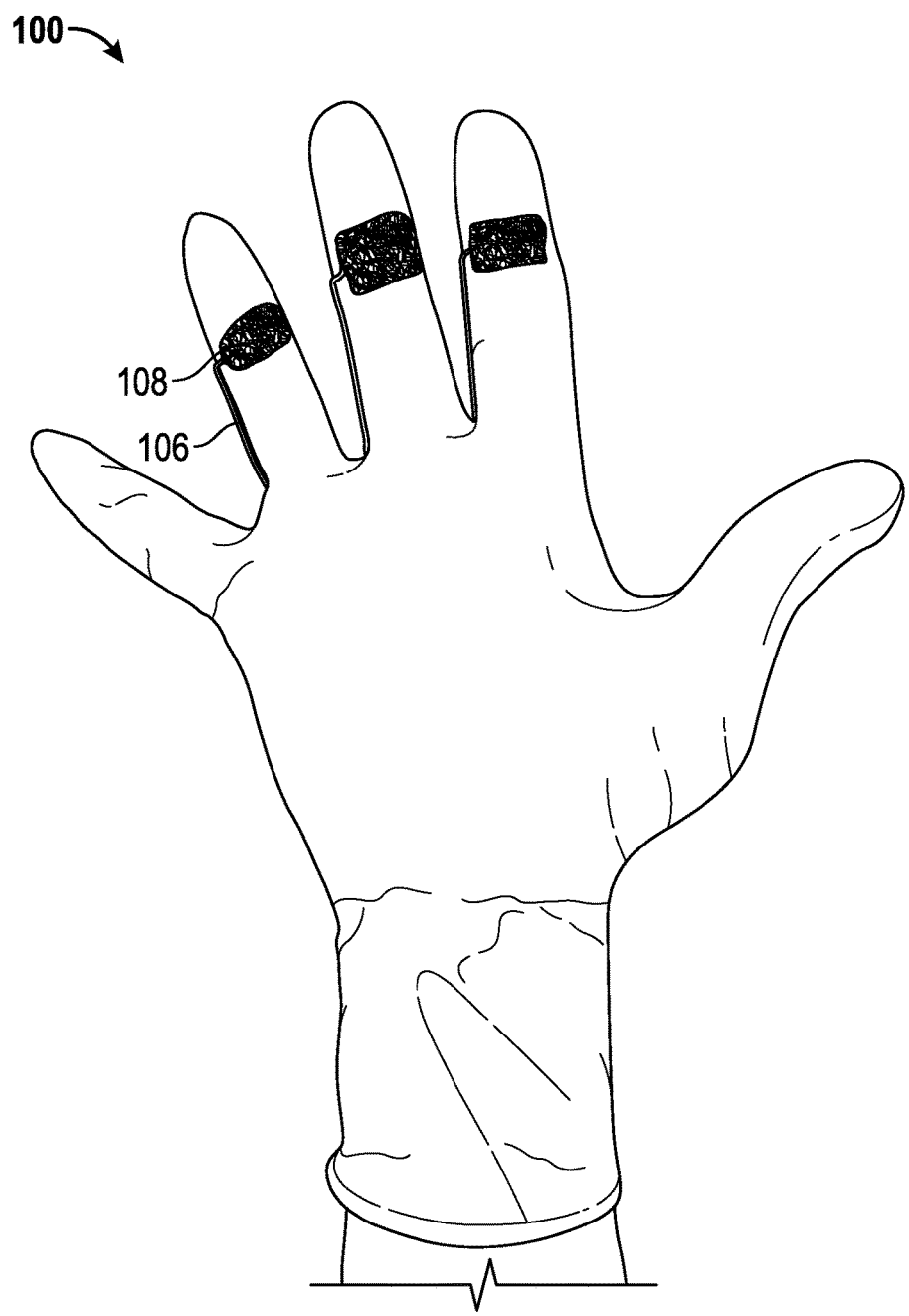
FIG. 2 is palmar view of an exemplary embodiment of a self-wetting sterile glove.

One exemplary embodiment is shown in FIGS. 1 and 2, which show distal and palmar views, respectively, of an exemplary device 100. As seen in FIG. 1, the device 100 comprises a bladder reservoir 102 with an injection port 104. Three flexible fluid conduits 106 extend from the reservoir 102 along the dorsal aspect of the glove to the base of the fingers. At that point, each flexible fluid conduit 106 is redirected to extend along the side of a digit. In the exemplary device, flexible fluid conduits 106 are seen to extend along each of the second, third, and fourth digit.

Turning now to FIG. 2, the flexible fluid conduits 106 are again seen to extend along each of the second, third, and fourth digits. However, FIG. 2 shows the arrangement from a palmar view of the exemplary device 100. From this view, it is seen that the flexible fluid conduits 106 are eventually directed in the palmar direction and terminate in fluid communication with the absorbent pads 108.

The moisture dispensing glove of the present invention comprises a glove with five digits that is preferably fabricated from relatively thin gauge elastomeric material. It is further preferable that the glove is either disposable or sterilizable and may be made in various sizes and of various lengths to extend the desired distance up the arm. One or more of the fluid reservoir, flexible fluid conduits and absorbent pads may be incorporated into the glove, or detachable, in any combination. If a component is detachable, the detachable component may be attached to a gloved hand by any suitable means, including by any suitable adhesive or mechanical means of attachment.

In some embodiments, all of the fluid reservoir, flexible fluid conduits and absorbent pads are not integral to the glove. In these embodiments, a user first puts a glove on their hand, and then installs the fluid reservoir, flexible fluid conduits and absorbent pads to a gloved hand. As indicated above, the fluid reservoir, flexible fluid conduits and absorbent pads may be attached and held in place on the gloved hand by any suitable means, including by any suitable adhesive or mechanical means of attachment, in any combination without limitation.

One skilled in the art will appreciate that the present invention can be practiced by other than the various embodiments and preferred embodiments, which are presented in this description for purposes of illustration and not of limitation, and the present invention is limited only by the claims that follow. It is noted that equivalents for the particular embodiments discussed in this description may practice the invention as well.

While various embodiments of the present invention have been described above, it should be understood that they have been presented by way of example only, and not of limitation. Likewise, the various diagrams may depict an example architectural or other configuration for the invention, which is done to aid in understanding the features and functionality that may be included in the invention. The invention is not restricted to the illustrated example architectures or configurations, but the desired features may be implemented using a variety of alternative architectures and configurations. Indeed, it will be apparent to one of skill in the art how alternative functional, logical or physical partitioning and configurations may be implemented to implement the desired features of the present invention. Also, a multitude of different constituent module names other than those depicted herein may be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the invention, whether or not such embodiments are described and whether or not such features are presented as being a part of a described embodiment. Thus the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, may be combined in a single package or separately maintained and may further be distributed across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives may be implemented without confinement to the illustrated examples. For example, block diagrams and their accompanying description should not be construed as mandating a particular architecture or configuration.

The invention claimed is:

1. A moisture dispensing system, comprising:
   a sterile surgical glove;
   a fluid reservoir containing a sterile fluid comprising sterile water or saline and attached to a dorsal aspect of the surgical glove when worn by a wearer; and
   an absorbent pad configured for attachment to a palmar aspect of a digit of said surgical glove when worn by a wearer, wherein said absorbent pad is in fluid communication with said fluid reservoir.

2. The moisture dispensing system of claim 1, comprising distinct absorbent pads configured for attachment to the palmer aspect of each of a plurality of digits of said surgical glove.

3. The moisture dispensing system of claim 1, comprising distinct absorbent pads configured for attachment to the palmer aspect of each of three digits of said surgical glove.

4. The moisture dispensing system of claim 1, comprising distinct absorbent pads configured for attachment to the palmer aspect of a second, third, and fourth digits of said surgical glove.

5. The moisture dispensing system of claim 1, wherein the absorbent pad is configured to attach to the palmer aspect of a digit of said surgical glove such that the absorbent pad is found in the region of a second and third metacarpophalangeal (MP) joints of a wearer.

6. The moisture dispensing system of claim 1, further comprising a fluid conduit extending from said fluid reservoir to said absorbent pad.

7. The moisture dispensing system of claim 6, wherein said fluid conduit comprises polyvinyl chloride tubing, polyisoprene rubber tubing, or nitrile rubber tubing.

8. The moisture dispensing system of claim 6, wherein said fluid conduit comprises a flexible solid material through which fluids pass by wicking action.

9. The moisture dispensing system of claim 1, wherein said fluid reservoir comprises an injection port for introduction of the sterile fluid into the fluid reservoir.

10. The moisture dispensing system of claim 1, wherein said fluid reservoir contains between about 5 ml to 50 ml of fluid.

11. The moisture dispensing system of claim 1, wherein the sterile fluid in said fluid reservoir flows to said absorbent pad without the aid of a pump.

12. The moisture dispensing system of claim 1, wherein said moisture dispensing device system is sterile.

13. A moisture dispensing glove, comprising:
a surgical glove having five digits;
a fluid reservoir containing a sterile fluid comprising sterile water or saline and located on a dorsal aspect of the glove; and
an absorbent pad attached to a palmar aspect of a digit, wherein said absorbent pad is in fluid communication with said fluid reservoir.

14. The moisture dispensing glove of claim 13, comprising distinct absorbent pads attached to the palmer aspect of each of a plurality of digits.

15. The moisture dispensing glove of claim 13, comprising distinct absorbent pads attached to the palmer aspect of each of three digits.

16. The moisture dispensing glove of claim 13, comprising distinct absorbent pads attached to the palmer aspect of a second, third, and fourth digits.

17. The moisture dispensing glove of claim 13, wherein the absorbent pad is attached to the palmer aspect of a digit such that the absorbent pad is found in the region of a second and third metacarpophalangeal (MP) joints of a wearer.

18. The moisture dispensing glove of claim 13, further comprising a fluid conduit extending from said fluid reservoir to said absorbent pad.

19. The moisture dispensing glove of claim 18, wherein said fluid conduit comprises polyvinyl chloride tubing, polyisoprene rubber tubing, or nitrile rubber tubing.

20. The moisture dispensing glove of claim 18, wherein said fluid conduit comprises a flexible solid material through which fluids pass by wicking action.

21. The moisture dispensing glove of claim 13, wherein said fluid reservoir comprises an injection port for introduction of the sterile fluid into the fluid reservoir.

22. The moisture dispensing glove of claim 13, wherein said fluid reservoir contains between about 5 ml to 50 ml of fluid.

23. The moisture dispensing glove of claim 13, wherein the sterile fluid in said fluid reservoir flows to said absorbent pad without the aid of a pump.

* * * * *